United States Patent [19]
Lane

[11] Patent Number: 5,735,857
[45] Date of Patent: Apr. 7, 1998

[54] PROSTHETIC GRIPPING INSTRUMENT

[75] Inventor: Richard A. Lane, Fort Wayne, Ind.

[73] Assignee: Bristol-Myers Squibb Co., New York, N.Y.

[21] Appl. No.: 686,169

[22] Filed: Jul. 22, 1996

[51] Int. Cl.⁶ ................................................. A61B 17/88
[52] U.S. Cl. ............................. 606/99; 606/207; 81/418
[58] Field of Search .......................... 606/207, 86, 99; 81/418, 387; 433/159

[56] References Cited

U.S. PATENT DOCUMENTS

| D. 340,979 | 11/1993 | Hersberger et al. | D24/133 |
|---|---|---|---|
| 2,631,585 | 3/1953 | Siebrandt | 606/207 X |
| 2,698,483 | 1/1955 | Berkowitz | 606/207 X |
| 3,857,389 | 12/1974 | Amstutz | 128/92 EC |
| 4,222,382 | 9/1980 | Antonsson et al. | 128/303 R |
| 4,642,121 | 2/1987 | Keller | 623/18 |
| 4,792,339 | 12/1988 | Tepi | 623/18 |
| 4,813,962 | 3/1989 | Deckner et al. | 623/23 |
| 4,896,661 | 1/1990 | Bogert et al. | 606/207 X |
| 4,919,153 | 4/1990 | Chin | 606/93 |
| 4,919,679 | 4/1990 | Averill et al. | 623/23 |
| 4,936,863 | 6/1990 | Hofmann | 623/23 |
| 4,993,410 | 2/1991 | Kimsey | 606/100 |
| 5,059,196 | 10/1991 | Coates | 606/99 |
| 5,064,427 | 11/1991 | Burkinshaw | 606/99 |
| 5,196,018 | 3/1993 | Willert et al. | 606/99 |
| 5,409,492 | 4/1995 | Jones | 606/86 |
| 5,476,466 | 12/1995 | Barrette et al. | 686/86 |
| 5,514,136 | 5/1996 | Richelsoph | 606/99 |
| 5,529,571 | 6/1996 | Daniel | 606/207 X |

FOREIGN PATENT DOCUMENTS

| 0 207 873 B1 | 7/1987 | European Pat. Off. | A61F 2/46 |
|---|---|---|---|
| 0 408 109 A1 | 1/1991 | European Pat. Off. | A61F 2/46 |
| 0 450 007 B1 | 9/1991 | European Pat. Off. | A61F 2/46 |
| 2615-097-A | 11/1988 | France | A61F 2/46 |
| 932366 | 7/1963 | United Kingdom | 606/207 |

OTHER PUBLICATIONS

Universal Modular Femoral Hip Component Extractor–Innomed, Inc.–c1995.

Primary Examiner—Michael H. Thaler
Attorney, Agent, or Firm—Margaret L. Geringer

[57] ABSTRACT

A prosthetic gripping instrument 10 for inserting or removing an orthopaedic product 1. The instrument 10 has a first gripping jaw 20 which is pivotally attached and a second gripping jaw 30 which is swivelably attached. This allows the instrument 10 to be used with a wide variety of orthopaedic products having varying geometries, such as various styles of hip stem implants or other surgical products.

9 Claims, 3 Drawing Sheets

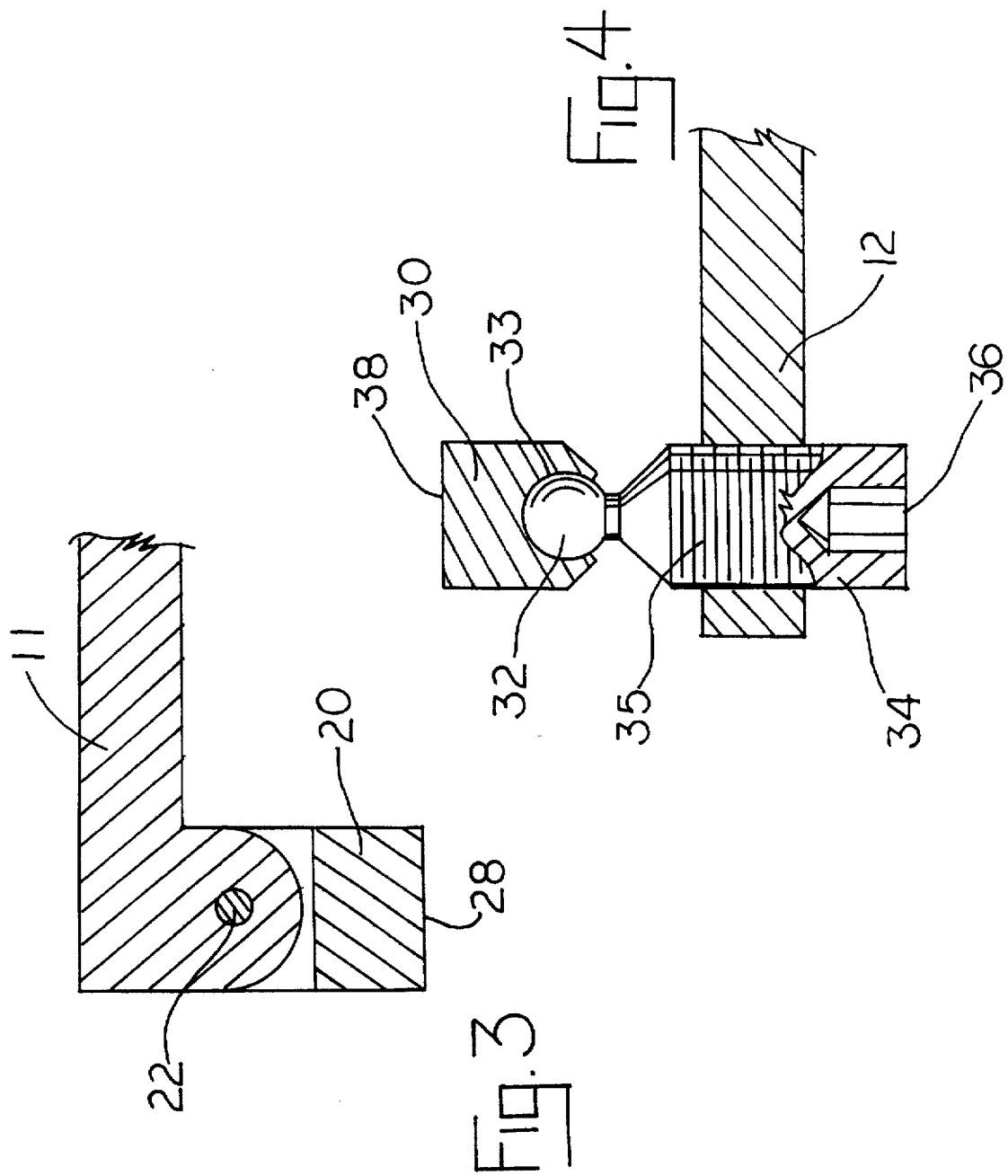

PROSTHETIC GRIPPING INSTRUMENT

FIELD OF THE INVENTION

This invention relates to the field of orthopaedic positioning instruments. In particular, this invention relates to such instruments for positioning implants or other surgical products.

BACKGROUND OF THE INVENTION

In the field of orthopaedics, it is known to utilize various styles of implant positioning instruments to either position or insert an implant or to remove an implant or other such surgical device. For example, many such instruments are secured to the implant or device to be inserted by threading a rod into a hole in the device, such as the following instruments for femoral hip implants: U.S. Pat. Nos. 4,936,863 or 4,919,679.

Other instruments are attached to the neck of a femoral prosthesis, such as in U.S. Pat. Nos. 5,064,427; 4,993,410; 4,792,339; and 4,642,121. In U.S. Pat. No. 5,476,466, a locator post is provided for insertion into a transverse hole in the proximal portion.

These positioning instruments are typically designed to accommodate a specific geometry on a particular product.

SUMMARY OF THE INVENTION

The present invention provides an orthopaedic positioning or gripping instrument for inserting or removing an orthopaedic product. The instrument has a first elongated arm and a second elongated arm interconnected by a connecting mechanism which allows the distal ends of each arm to be moved toward or away from each other. One of the distal ends has a first gripping jaw which is pivotally attached thereto, while the other of the distal ends has a second gripping jaw which is swivelably attached. This allows the instrument to be used with a wide variety of orthopaedic products, such as hip stem implants having varying geometries. The pivot and swivel jaws enable the instrument to grip two opposite surfaces of a product, and enables those surfaces to have various configurations, angles, dimensions. The combination of the pivot jaw and swivel jaw provides control and stability.

Accordingly, it is an advantage of the present invention to provide a novel instrument for gripping a wide variety of orthopaedic products of varying shapes and sizes.

Another advantage of the invention is to provide a gripping instrument which includes a pivot jaw and a swivel jaw to provide adjustability to grip orthopaedic products having various shapes and sizes.

A further advantage of the invention is to provide a simple instrument for gripping an orthopaedic product.

Still other advantages of the invention will become apparent upon reference to the accompanying drawings.

BRIEF DESCRIPTION OF THE DRAWINGS

FIG. 3 is a cross-sectional view of the first pivotal jaw of the instrument of FIG. 1.

FIG. 4 is a partial cross-sectional view of the second swivelable jaw of the instrument of FIG. 1.

DESCRIPTION OF THE PREFERRED EMBODIMENT

Figure 1:
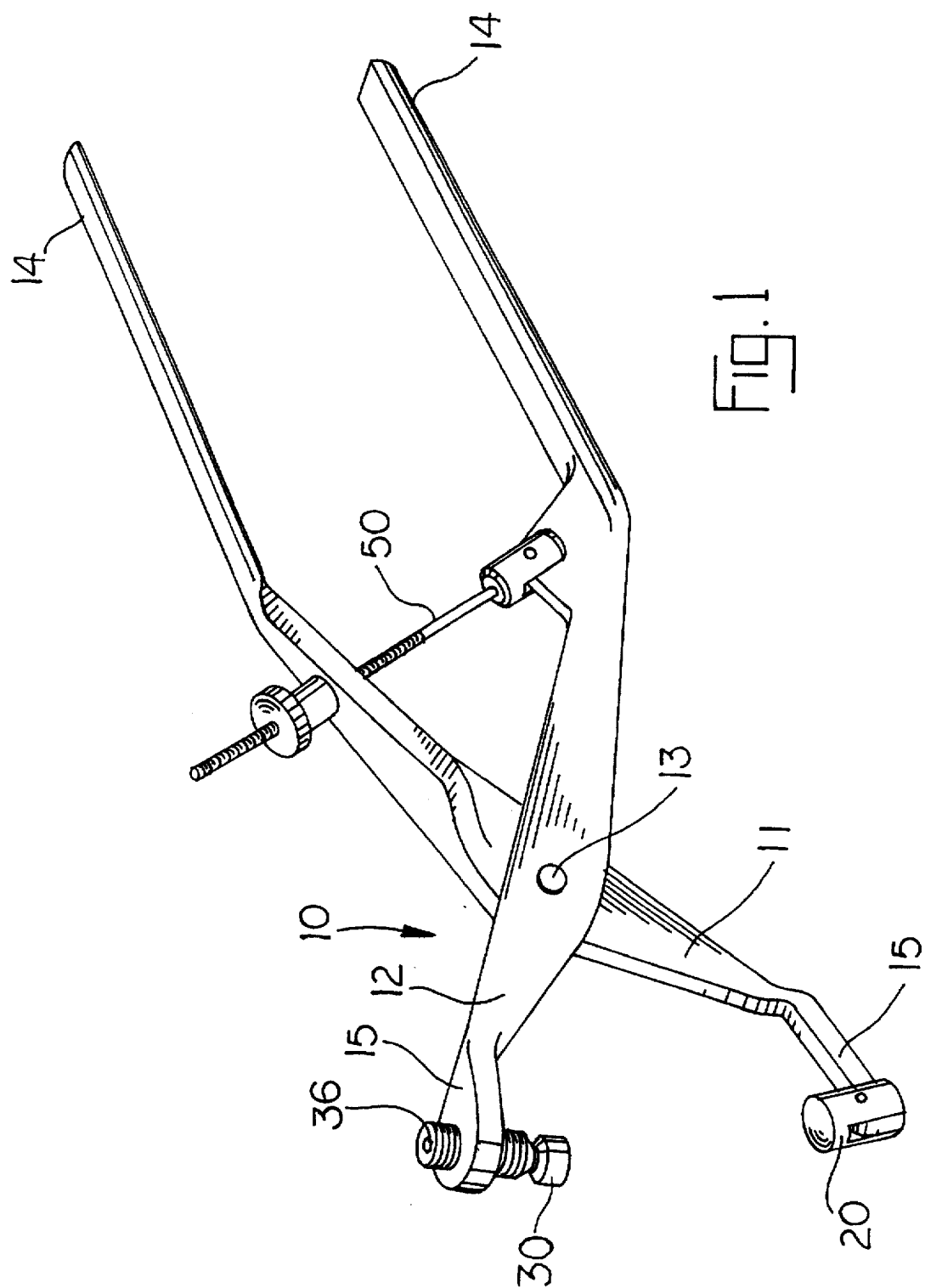
FIG. 1 is a perspective view of the instrument of the present invention.

The preferred embodiment described herein is not intended to be exhaustive or to limit the invention to the precise form disclosed. Rather it is chosen and described to best explain the invention so that others skilled in the art might utilize its teachings.

Accordingly, FIGS. 1–4 illustrate a preferred embodiment of a gripping instrument in accordance with the present invention. This invention relates to instruments for gripping or positioning an orthopaedic implant or other suitable surgical device. The invention will be described for use with a prosthetic femoral hip implant; however, it is understood that the invention is not limited thereto, and that the instrument could be adapted for positioning other implants or surgical devices.

The instrument 10 includes a first elongated arm 11 and a second elongated arm 12 interconnected by a connecting mechanism 13. Each arm 11 and 12 has a proximal end 14 and a distal end 15. The connecting mechanism allows the distal ends of each arm to be moved toward or away from each other. The connecting mechanism 13 utilizes a connecting pivot pin member. One of the distal ends 15 has a first gripping jaw 20 which is pivotally attached thereto. The other of the distal ends 15 has a second gripping jaw 30 which is swivelably attached.

The first jaw 20 pivots about an axis of a pivot pin 22 which interconnects the first jaw 20 to the one distal end 15. The second jaw 30 swivels about a spherical member 32 which is interconnected to the other distal end 15. The spherical member 32 is positioned in a complementary spherical cavity 33. The other distal end 15 includes either the spherical member or the spherical cavity therein with the other of the mating spherical member and cavity being provided on the swivelable jaw. The other distal end 15 may include a separate connecting member 34 attached thereto which includes the spherical member or mating cavity. FIG. 4 illustrates the spherical member 32 on the connecting member 34, with the cavity or socket 33 in the second jaw 30. The connecting member 34 may be conveniently attached to the other distal end 15 via threads 35. Hex socket 36 is provided in connecting member 34 for threading member 34 into the other distal end 15. The second jaw 30 may be swaged onto spherical member or ball 32, although any suitable method may be used to provide this swivelable ball and socket joint 32 and 33, thus allowing swivelable motion about the spherical member 32.

Figure 2:
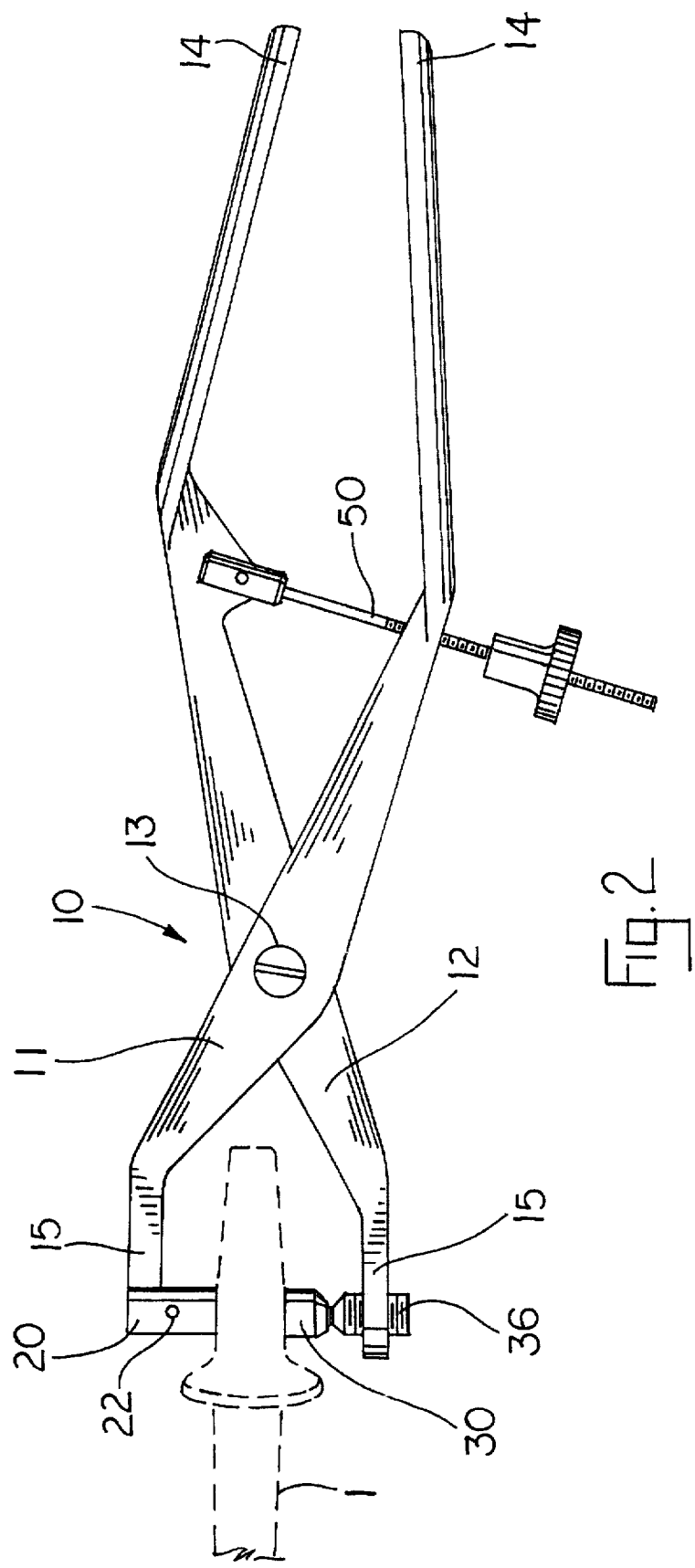
FIG. 2 is a side view of the instrument of FIG. 1, shown gripping a femoral implant device.

Each jaw 20 and 30 has a surface 28 and 38, respectively, for gripping opposite sides of the product 1. In FIG. 2, the instrument 10 is gripping the anterior and posterior surfaces of a femoral stem implant between the neck and collar of the implant. The instrument 10 may be advantageously used to grip or hold the femoral implant while inserting the stem into bone cement. The swivel and pivot jaws are able to adjust to the geometry of the implant to grip it securely. The pivot jaw 20 prevents rotation in the medial/lateral plane of the femoral implant when the instrument 10 is gripping the anterior and posterior surfaces of a femoral implant as shown in FIG. 2. The swivel jaw provides multidirectional adjustability. The surfaces 28 and 38 may be flat, as shown, or contoured (not shown), as desired. The instrument is preferably made of metal, such as stainless steel, although any suitable material may be utilized. The surfaces 28 and 38 may include a nonmetallic material to protect the implant being gripped or to improve the security of the grip. This nonmetallic material may be either a nonmetallic cap over the gripping surface or a nonmetallic o-ring embedded in the surface of the jaw or a nonmetallic coating or layer (not shown). Silicone or any other suitable nonmetallic material may be used. Alternatively, the whole jaw may be made of a nonmetallic material, if desired, and as such, manufactured by any suitable method.

The first and second elongated arms 11 and 12 may include an adjustable locking mechanism 50 therebetween to control the amount of separation between the distal ends. A threaded locking mechanism 50 as shown in FIGS. 1 and 2 may be used for this purpose, although any suitable locking mechanism can be used.

While this invention has been described in terms of a particularly advantageous embodiment, those skilled in the art can appreciate that modifications can be made without departing from the spirit and scope of this invention.

I claim:

1. A prosthetic gripping instrument for inserting or removing an orthopaedic product, the instrument comprising a first elongated arm and a second elongated arm, each arm having a proximal end and a distal end, and wherein the arms are interconnected by a connecting mechanism to allow the distal ends of each arm to be moved toward or away from each other, one of said distal ends has a first gripping jaw which is pivotally attached thereto and the other of said distal ends has a second gripping jaw which is swivelably attached thereto, wherein the first jaw is limited to pivotal movement in a single plane about an axis of a pivot pin which interconnects the first jaw to the one distal end, said axis being nonperpendicular to a first gripping surface of the first jaw, and wherein said swivelable second jaw provides multiplanar adjustability.

2. The instrument of claim 1 wherein the second jaw swivels about a spherical member which is interconnected to the other distal end.

3. The instrument of claim 2 wherein the spherical member is positioned in a complementary spherical cavity.

4. The instrument of claim 3 wherein the other distal end includes a connecting member attached thereto wherein the connecting member includes one of the spherical member or the spherical cavity therein.

5. The instrument of claim 4 wherein the connecting member is threadably attached to the other distal end.

6. The instrument of claim 1 wherein said second jaw has a second gripping surface, wherein said first and second surfaces are adapted for gripping opposite sides of the product.

7. The instrument of claim 6 wherein the surfaces for gripping opposite sides of the product comprise a nonmetallic material.

8. The instrument of claim 1 wherein the connecting mechanism is a connecting pivot pin member.

9. The instrument of claim 1 wherein the first and second elongated arms include an adjustable locking mechanism therebetween to control the amount of separation between the distal ends.

* * * * *